United States Patent
Botich

(10) Patent No.: US 9,119,939 B2
(45) Date of Patent: Sep. 1, 2015

(54) ROTATABLE HYPODERMIC NEEDLE AND METHOD OF USE

(71) Applicant: Michael J. Botich, Reno, NV (US)

(72) Inventor: Michael J. Botich, Reno, NV (US)

(*) Notice: Subject to any disclaimer, the term of this patent is extended or adjusted under 35 U.S.C. 154(b) by 0 days.

(21) Appl. No.: 14/025,802

(22) Filed: Sep. 12, 2013

(65) Prior Publication Data

US 2015/0073382 A1    Mar. 12, 2015

(51) Int. Cl.
| | | |
|---|---|---|
| A61B 17/34 | (2006.01) | |
| A61M 25/06 | (2006.01) | |
| A61M 25/02 | (2006.01) | |
| A61M 5/158 | (2006.01) | |

(52) U.S. Cl.
CPC ........ A61M 25/0631 (2013.01); *A61B 17/3496* (2013.01); *A61M 2005/1581* (2013.01); *A61M 2005/1585* (2013.01); *A61M 2025/0253* (2013.01)

(58) Field of Classification Search
CPC ............ A61M 5/158; A61M 25/0612; A61M 2005/1585; A61M 2025/0266; A61M 5/3202; A61M 5/3293; A61M 25/0637; A61M 2005/1586; A61M 25/02; A61M 5/1626; A61M 5/321; A61M 2005/1581
USPC ................. 604/263, 192, 177, 198, 162, 174, 604/164.08, 171, 164.04, 180
See application file for complete search history.

(56) References Cited

U.S. PATENT DOCUMENTS

| | | | |
|---|---|---|---|
| 4,631,058 A * | 12/1986 | Raines | ........................... 604/263 |
| 4,994,034 A | 2/1991 | Botich et al. | |
| 5,188,599 A | 2/1993 | Botich et al. | |
| 5,407,431 A | 4/1995 | Botich et al. | |
| 5,685,863 A | 11/1997 | Botich et al. | |
| 5,788,677 A | 8/1998 | Botich et al. | |
| 5,800,395 A | 9/1998 | Botich et al. | |
| 5,858,001 A * | 1/1999 | Tsals et al. | ..................... 604/135 |
| 5,879,330 A * | 3/1999 | Bell | ........................... 604/93.01 |
| 5,921,969 A * | 7/1999 | Vallelunga et al. | ........... 604/263 |
| 5,951,522 A * | 9/1999 | Rosato et al. | ................. 604/177 |
| 6,004,278 A | 12/1999 | Botich et al. | |
| 6,039,713 A | 3/2000 | Botich et al. | |
| 6,077,244 A | 6/2000 | Botich et al. | |
| 6,096,005 A | 8/2000 | Botich et al. | |
| 6,123,688 A | 9/2000 | Botich et al. | |
| 6,179,812 B1 | 1/2001 | Botich et al. | |
| D445,183 S | 7/2001 | Botich et al. | |
| 6,267,750 B1 * | 7/2001 | Utterberg | ...................... 604/264 |
| 6,398,743 B1 | 6/2002 | Botich et al. | |
| 6,436,070 B1 | 8/2002 | Botich et al. | |
| 6,461,362 B1 | 10/2002 | Botich et al. | |

(Continued)

*Primary Examiner* — Nicholas Lucchesi
*Assistant Examiner* — William Carpenter
(74) *Attorney, Agent, or Firm* — John D. Long, Esq.; Long & Chybik

(57) ABSTRACT

One possible embodiment of the invention could be a hypodermic needle that rotatably connects to a shield comprising a hypodermic needle denoted into a distal needle portion and a proximal needle portion, the distal needle portion's injection aperture continuously connected to the proximal needle portion's connection aperture; a shield that comprises at least a skin pad portion, the proximal needle portion being rotatably held within a portion of the shield in a manner that allows the distal needle portion to be moved between an operative position, wherein the distal needle portion descends downward and away from a bottom of the skin pad portion to hold the needle tip away from the skin pad portion to a stored position that has the needle tip of the distal needle portion placed proximate to the skin pad portion.

14 Claims, 24 Drawing Sheets

(56) References Cited

U.S. PATENT DOCUMENTS

| | | | |
|---|---|---|---|
| 6,500,155 B2 * | 12/2002 | Sasso | 604/177 |
| 6,524,276 B1 | 2/2003 | Botich et al. | |
| 6,537,255 B1 * | 3/2003 | Raines | 604/177 |
| 6,540,732 B1 | 4/2003 | Botich et al. | |
| 6,547,762 B1 | 4/2003 | Botich et al. | |
| 6,569,115 B1 | 5/2003 | Botich et al. | |
| 6,641,555 B1 | 11/2003 | Botich et al. | |
| 6,676,633 B2 * | 1/2004 | Smith et al. | 604/110 |
| 6,719,721 B1 * | 4/2004 | Okazaki et al. | 604/110 |
| 6,752,798 B2 | 6/2004 | Botich et al. | |
| 6,786,875 B2 | 9/2004 | Botich et al. | |
| 6,921,391 B1 | 7/2005 | Botich et al. | |
| 6,945,960 B2 | 9/2005 | Botich et al. | |
| 6,969,372 B1 * | 11/2005 | Halseth | 604/164.08 |
| 7,056,306 B1 | 6/2006 | Botich et al. | |
| 7,090,656 B1 | 8/2006 | Botich et al. | |
| 7,097,633 B2 | 8/2006 | Botich et al. | |
| 7,153,276 B2 | 12/2006 | Botich et al. | |
| 7,229,434 B2 * | 6/2007 | Wang | 604/263 |
| 7,300,416 B2 | 11/2007 | Botich et al. | |
| 7,329,238 B2 | 2/2008 | Botich et al. | |
| 7,338,469 B2 | 3/2008 | Botich et al. | |
| 7,431,713 B2 * | 10/2008 | Harris et al. | 604/263 |
| 7,458,962 B2 | 12/2008 | Botich et al. | |
| 7,513,887 B2 | 4/2009 | Botich et al. | |
| 7,524,306 B2 | 4/2009 | Botich et al. | |
| 7,527,607 B2 | 5/2009 | Botich et al. | |
| 7,660,615 B2 * | 2/2010 | VanAntwerp et al. | 600/316 |
| 7,691,083 B2 | 4/2010 | Botich et al. | |
| 7,753,887 B2 | 7/2010 | Botich et al. | |
| 7,776,016 B1 * | 8/2010 | Halseth et al. | 604/162 |
| 7,927,317 B2 * | 4/2011 | Perouse et al. | 604/263 |
| D687,547 S * | 8/2013 | Wang | D24/130 |
| 8,500,703 B2 * | 8/2013 | Lambert | 604/263 |
| 2002/0072716 A1 * | 6/2002 | Barrus et al. | 604/192 |
| 2002/0111581 A1 * | 8/2002 | Sasso | 604/93.01 |
| 2002/0173749 A1 * | 11/2002 | Wagner et al. | 604/177 |
| 2003/0069546 A1 * | 4/2003 | Sandstrom et al. | 604/263 |
| 2003/0083624 A1 * | 5/2003 | Smith et al. | 604/177 |
| 2003/0105449 A1 * | 6/2003 | Raines | 604/506 |
| 2003/0163098 A1 * | 8/2003 | Fleury et al. | 604/263 |
| 2005/0080386 A1 * | 4/2005 | Reid | 604/263 |
| 2006/0041234 A1 * | 2/2006 | Wang | 604/263 |
| 2006/0161109 A1 * | 7/2006 | Huet | 604/174 |
| 2008/0177234 A1 * | 7/2008 | Keaton et al. | 604/177 |
| 2009/0163875 A1 * | 6/2009 | Hiraoka et al. | 604/192 |
| 2010/0010451 A1 * | 1/2010 | Kashmirian et al. | 604/192 |
| 2010/0312183 A1 * | 12/2010 | Halseth et al. | 604/116 |

* cited by examiner

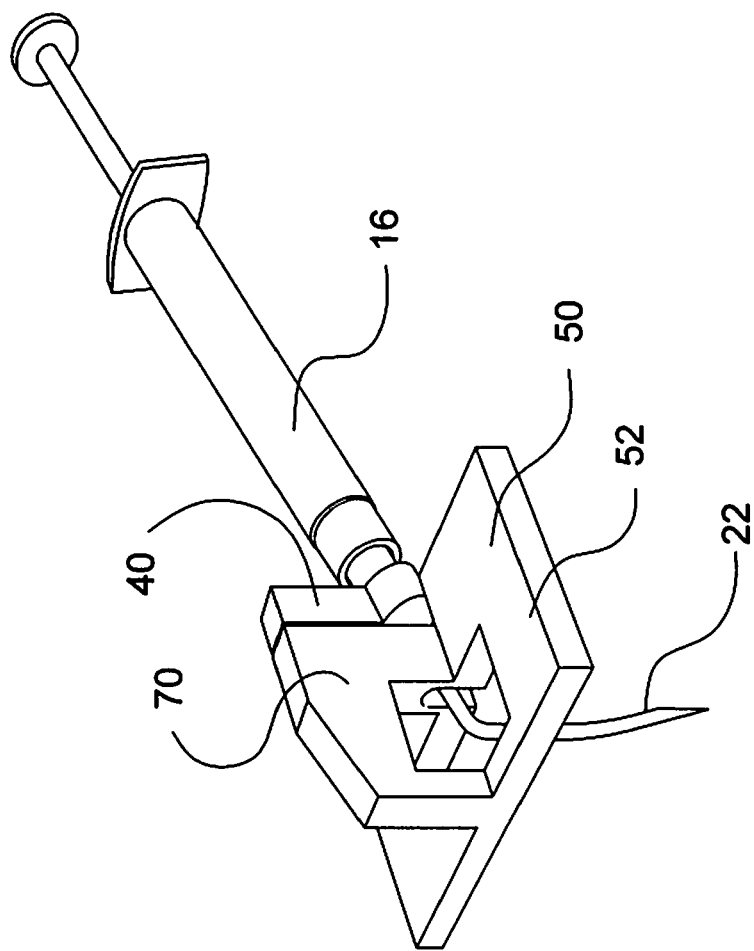

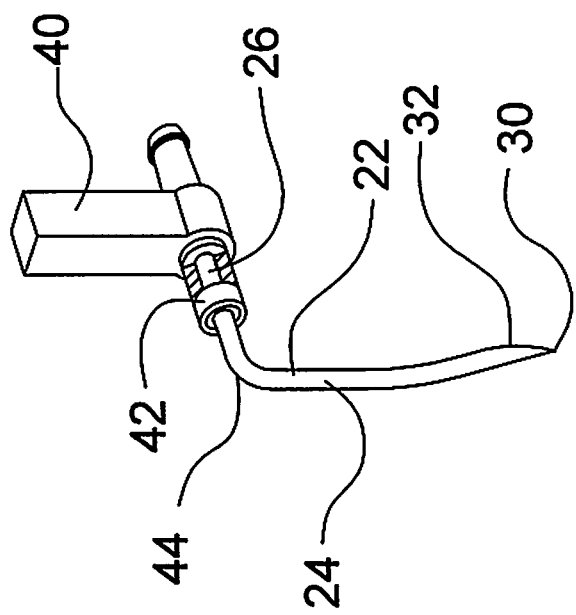

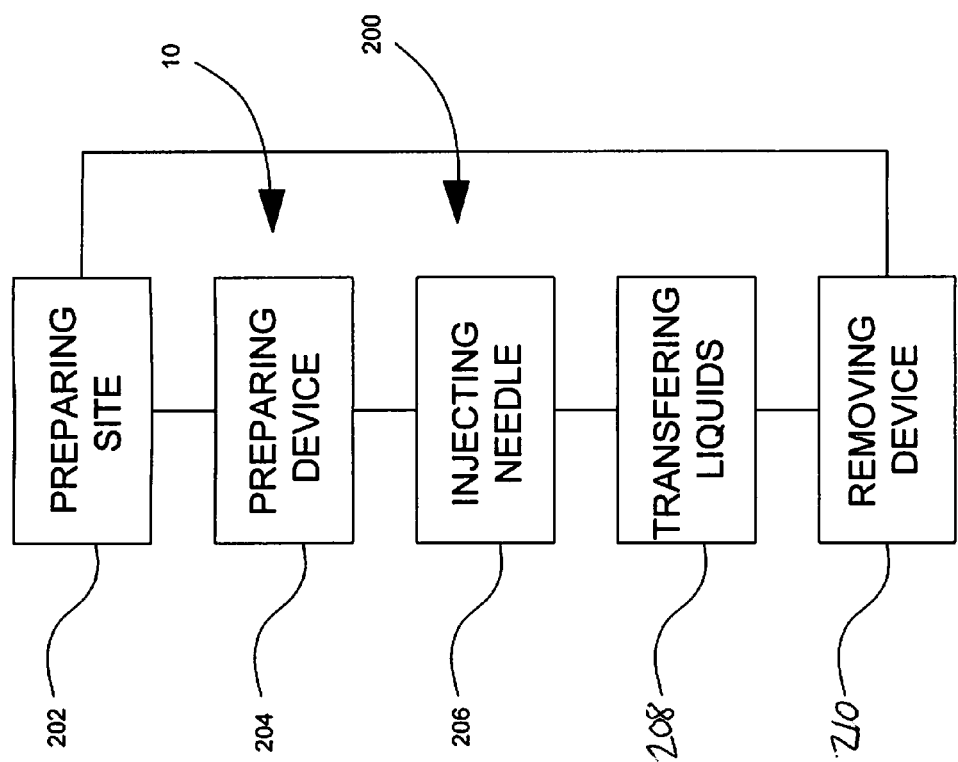

ROTATABLE HYPODERMIC NEEDLE AND METHOD OF USE

STATEMENT REGARDING FEDERALLY SPONSORED RESEARCH OR DEVELOPMENT

Not Applicable

REFERENCE TO A "MICROFICHE APPENDIX"

Not Applicable

FIELD OF THE INVENTION

The present invention relates to those hypodermic needles that may incorporate a safety mechanism that substantially covers or otherwise sheathes the needle's injection end to reduce the possibility of post-use accidental injection. More particularity to those hypodermic needles with safety mechanisms that substantially use a rotational motion post-use to cover or sheath the needle's injection end

BACKGROUND

Hypodermic needles have been combined with a variety of safety devices to help prevent unwanted/accidental needle-stick injuries after a needle has been used in its intended purpose (e.g., post-use.) Once type of hypodermic needle that has been fitted with such safety devices is the Huber-type hypodermic needle ("Huber needle".) The Huber needle is generally used in combination with a subcutaneously implanted port or septum located within one or more various areas of a patient such as the arm, side or buttocks to provide intravenous connections for repetitive and/or lengthy infusions, extractions, or the like (e.g., lasting between several minutes to a few hours) such as those involved in chemotherapy, dialysis, etc. The port or septum directly connects with one of the patient's blood vessel (e.g., a vein) in a manner that allows the port's hollow interior to be in continuous communication with an interior of the attached blood vessel.

One aspect of the Huber needle is that it presents the injection aperture or opening on the side of the needle proximate to a tip of the needle unlike other hypodermic needles having the aperture located directly at the very injection tip itself. In this manner, the Huber injection aperture will create a self-sealing slit opening in the port when injected into the skin injection site/port. When the Huber needle is withdrawn from the port, the slit opening in the port will generally self-close or self-seal to substantially keep contents within the port's hollow interior from leaking to outside of the port.

If a non-Huber type hypodermic needle (e.g., having an injection aperture on its injection tip) is used to penetrate through an injection site into the port/septum, the non-Huber needle could cause the tip-based injection aperture to punch open a non-slit or open type hole, rather than open a closable slit opening, into the port. When the non-Huber needle is subsequently removed from the port, this punched open hole could allow the contents within the port's hollow interior to leak outside of the port. Additionally, the repeated use of a non-Huber type hypodermic needle upon the port could significantly shorten the port's operational lifespan of that port requiring a greater replacement frequency for the port. Generally, Huber hypodermic needle usage substantially allows a much greater number of connections per the port/septum than could be obtained with the usage of a non-Huber hypodermic needle.

Another characteristic of the Huber needle is that it may be bent into two portions, a distal (or injection) portion and proximal (or connection) portion, wherein the proximal portion is generally oriented to be perpendicular to the distal portion. The proximal portion may be connected to a shield that may be grasped by a health care operator to generally move and contact/inject the proximal portion with the septum or port. The distal needle portion may project downward and away from the underside or bottom of the shield in a perpendicular manner so that when an operator grasps shield (e.g., by a vertical blade projecting upward from the top of the shield), the bottom of the shield may then rested upon the skin of the patient that is covering the septum/port after the distal needle portion contacts (e.g., injected into) the septum or port to provide intravenous connection.

Although current health and safety standards for the Huber type needles generally do not mandate safety features to prevent accidental needle-stick of health care professionals (and others), there are available various anti-needle stick devices applied to Huber type needles that may allow the Huber type needle be withdrawn into a safety device such as a sheath structure (or conversely the sheath structure may be drawn over the Huber type needle) to allow for safe disposal. Generally, these Huber type needle anti-stick safety devices may be seen as bulky: cumbersome to use; and generally fail to make use of the Huber needle's bent shape.

What could be needed is a hypodermic needle that may generally employ a bent configuration that denotes a distal (injection) needle portion and a proximal (connection) needle portion, the proximal needle portion substantially being rotatably attached to a shield to allow the shield to act as an anti-needle stick device. Accordingly, an rotational movement could be to imparted to a needle/shield combination that substantially causes the needle's tip (of the distal needle portion) to move from an operative position (e.g., wherein the distal needle portion extends downward in a perpendicular manner from a bottom of the shield) to being placed next to (e.g., and at least partially covered by) the bottom of the shield (e.g., into a stored or storage position) to provide an anti needle-stick capability for safe disposal. A generally reverse rotational movement could also be employed to move the needle tip initially located in the stored position (e.g., next to the shield bottom) to its operational position for suitable use.

SUMMARY OF ONE EMBODIMENT OF THE INVENTION

Advantages of One or More Embodiments of the Present Invention

The various embodiments of the present invention may, but do not necessarily, achieve one or more of the following advantages:

to provide a hypodermic needle that is rotatably attached to a shield wherein one portion of the hypodermic needle is rotated to move another portion of the hypodermic needle between an operative position (e.g., wherein the distal needle portion extends downward in a perpendicular manner from the shield bottom) to a stored position (e.g., the needle tip is next to and/or at least partially covered by the bottom of the shield);

the ability to have a hypodermic needle that is rotatably attached to a shield, the shield bottom further comprising of a laminate pad wherein the needle tip in the stored position resides with a cutout of the laminate pad;

to provide a laminate pad having a releasable cover that is removed to expose a cutout to allow a tip of a hypodermic needle to rotatably connected to a shield to move from a stored position in the cutout into an operating condition;

to provide a hypodermic needle that is rotatably attached to a shield whose bottom has a laminate pad wherein the needle tip in the stored position resides with a cutout of the laminate pad that is otherwise covered by a releasable cover;

the ability to have a hypodermic needle rotatably attached to a shield, the needle being rotated to move a needle tip up into the shield bottom to provide an anti-needle stick capability;

to provide a bent hypodermic needle that is rotatably attached to a shield, the needle being rotated to move a respective needle tip from one side (e.g. right side) of the bottom of the shield (e.g., an unused first storing position) to an operative position, then when after the needle has been used, the rotational movement is continued to move the needle tip from an operative position to a second side (e.g. left side) of the bottom of the shield to a "used" and second stored position;

to provide a bent hypodermic needle that is rotatably attached to a shield, the bent hypodermic needle being rotated to move a respective needle tip from one side (e.g., left) of the bottom of the shield (e.g., a storing position) to an operative position, then when after the needle has been used, a counter or converse rotational movement is then used to move the needle tip from an operative position to back to one side (e.g. left side) of the bottom of the shield to the storing position for disposal:

the ability to have a hypodermic needle rotatably connected with a shield, the needle being bent into a distal (injection) needle portion and a proximate (connection) needle portion, the proximal and distal needle portions having an obtuse angular relationship with one another, this obtuse angular relationship allowing the distal needle portion be rolled up into the shield having a significantly smaller that shield that would have to be used if the angular relationship was perpendicular between the distal and proximal needle portions; and to provide a hypodermic needle bent into distal needle and proximate needle portions, the portions maintaining an obtuse angular relationship between themselves, the proximal needle portion being in an oblique angular relationship with the shield to allow the distal needle portion be rolled into the shield of a smaller size and thickness than if the angular relationship between the needle portions was perpendicular.

These and other advantages may be realized by reference to the remaining portions of the specification, claims, and abstract.

Brief Description of One Embodiment of the Present Invention

One possible embodiment of the invention could be a hypodermic needle that rotatably connects to a shield comprising: a hypodermic needle bent into a distal needle portion and a proximal needle portion, the distal needle portion further having a needle tip; a shield that comprises a vertical blade and a skin pad portion, the vertical blade projecting outward from a top of the skin pad portion, the proximal needle portion being rotatably held within a portion of the shield in a manner that allows the distal needle portion to be moved between an operative position, where the distal needle portion is perpendicular to and descends downward and away from the skin pad portion to hold the needle tip away from the skin pad portion to a stored position where the needle tip of the distal needle portion is placed next to the skin pad portion.

Another possible embodiment of the invention could be a process or method for operating a hypodermic needle that is rotatably held by a shield, comprising of the following steps: providing a hypodermic needle and a shield, the needle being bent into a distal needle portion and a proximal needle portion, the shield rotatably holds the proximal needle portion to be allow the distal needle portion to be move between an operative position, where the distal needle portion is perpendicular to and descends downward and away from the skin pad portion to a stored position where a needle tip of the distal needle portion is placed next to skin pad portion; rotating the proximal needle portion relative to the shield; and moving the distal needle portion between an operative and stored positions.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

FIG. 2A is substantially a cutaway view of one embodiment of syringed-based version of the present invention.

FIG. 3 is substantially a cutaway perspective view of one embodiment of handle and perpendicularly angled hypodermic needle combination of the present invention.

FIG. 12A is substantially an elevation end view showing one embodiment of the locking mechanism of the present invention to hold the needle in position relative to the shield, the position being operating position.

FIG. 5A is substantially a cutaway side elevation view of one possible embodiment of the present invention wherein the needle generally folds along the length of the shield, showing the needle in the operating position.

FIG. 16 is substantially a flow chart showing one possible process or method for operating the present invention.

DESCRIPTION OF CERTAIN EMBODIMENTS OF THE PRESENT INVENTION

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

Figure 1:
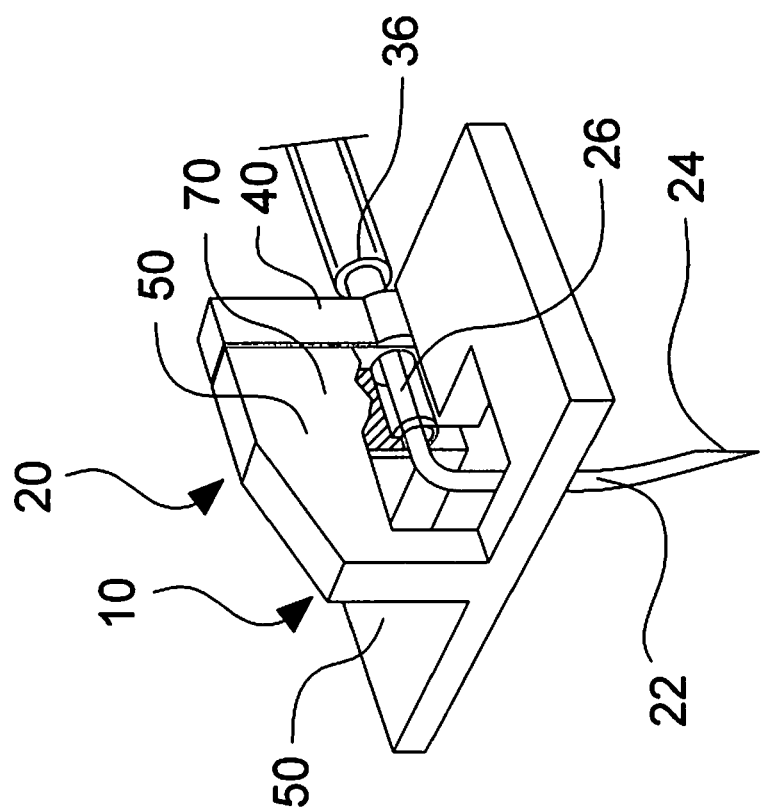
FIG. 1 is substantially a perspective cutaway view of one embodiment of perpendicularly angled hypodermic needle version of the present invention.

The present invention 10 could comprise of a hypodermic needle rotatable connected to a shield 20 to substantially provide an anti-needle-stick capability and a method or process for its use 200. As substantially shown in FIG. 1, the hypodermic needle rotatable connected to a shield 20 could comprise of a bent hypodermic needle 22 attached to a handle 40, the handle 40 being rotatably connected to a shield 50.

In one possible embodiment, the invention 10 could comprise of a hypodermic needle 20 that rotatably connected to a shield 50. The needle 20 in at least one embodiment could be bent into a distal (e.g., injection) needle portion 24 and a proximate (e.g. connection) needle portion 26 (e.g., as substantially found in a Huber type hypodermic needles.) The distal needle portion 24 could have a slight curvature as well unique bevel that may facilitate a creation of a practically re-sealable slit-type injection into a septum (not shown) as provided by such a Huber type needle. Proximate to an needle tip 30 of the distal needle portion 24 could be an injection aperture 32 that could be used to connect the septum or port (not shown) to a hollow interior 34 of the needle (as substantially provided by a Huber needle.) The needle's hollow interior 34 could further continuously connect the injection aperture 32 with a connection aperture 36 of the proximal needle portion 26.

In one version, a needle angle 28 between the two needle portions could be seen as being ninety (90°) degrees substantially establishing a perpendicular angular relationship between the distal and proximal needle portions 22, 24. When rotatably attached to the shield 50, the distal needle portion 24 may be kept at a parallel relationship with a top 54 of a skin pad portion 52 of the shield 50.

Figure 2:
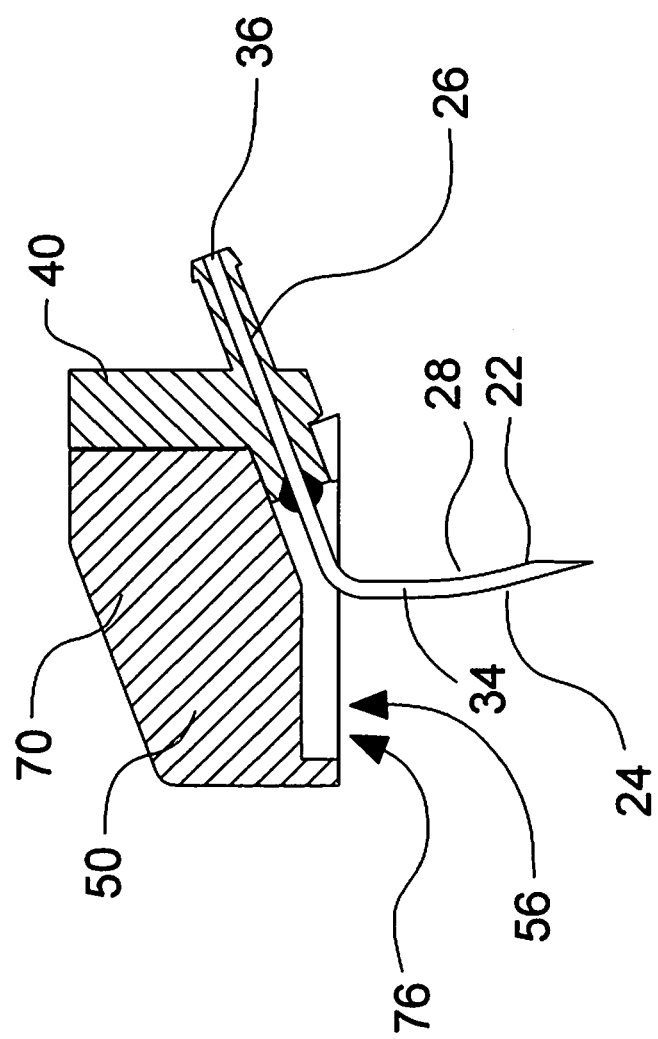
FIG. 2 is substantially a cutaway elevation view of one embodiment of obtuse angled hypodermic needle version of the present invention.

In another version, as substantially shown in FIG. 2, a needle angle 28 could be generally greater than ninety (90°) degrees and less than a one-hundred-and-eighty (180°) degrees to generally provide an obtuse angular relationship between the distal needle portion 24 and the proximal needle portion 26 to substantially establish an obtuse angular relationship between the distal and proximal needle portions 22, 26. As allowed by the bent hypodermic needle's obtuse angular relationship, the needle tip 30, in the stored position 14, may be found in a cutout 76 that could terminate in a location that is more towards to the skin pad portion's forward edge 62 rather than the side edge termination of a cutout 75 for a bent hypodermic needle 22 having a perpendicular relationship. This obtuse relationship could result in the width of the shield 50 being smaller that could that a shield used with a rotatably connected bent hypodermic needle 22 with a perpendicular needle portion relationship.

Additionally, the bent hypodermic needle's obtuse angular relationship could require the proximal needle portion 26 to have an oblique angular relationship with the top 54 of the skin pad portion. This oblique angular relationship of hem hypodermic needle 22 to shield 50 could place distal needle portion 24 with a parallel orientation with the bottom 56 when rotated into the stored position 14. This parallel orientation could allow the shield 50 to be made of a smaller thickness that the use of a perpendicular bent hypodermic needle 22 whose distal needle portion would not have the benefit of a parallel orientation (e.g., angled relationship to the bottom 56 when placed in the stored position 14.

The connection aperture 36 could end in a standard "Luer-lock" type thread connector on the rearward end. This thread connector is generally standardized throughout the medical device field and may be used on a myriad of devices ranging from syringes to infusion pumping devices to IV bags. Another version (not shown) of the connector could have the distal needle portion 24 have on its outside surface a radial barbed feature designed for connecting to a standard IV tube. Yet another version (not shown) could have an adapter component that could provide the bent hypodermic needle 22 with a wide variety of connection configurations that generally allows the invention 10 to be attached to wide variety of intravenous delivery/extraction medical systems. Such connectors could allow a flexible hollow tube or like (e.g., an intravenous system) to be continuously connected to a "Luer-lock" type thread connector of the invention.

As shown in FIG. 2A, it should also be noted that intravenous delivery/extraction medical systems could include a syringe 16 and that the present invention 10 can be used in combination in connection with a syringe and be within the preview of the invention 10. In such an embodiment, the "Luerlock" type thread connector of the bent hypodermic needle 22 could be angled upwards that places the syringe at an upper angled orientation to the shield 50. After the invention is used, the syringe may be removed to allow the distal portion 24 to be moved to a stored or storage position proximate the underside of the shield 50.

As substantially shown in FIG. 3, a handle 40 be attached to the bent hypodermic needle 22 at its proximal needle portion 26. The handle 40 could be of molded plastic (or other suitable material) configured with a cylindrical portion 42 at one end of the handle 40. The cylindrical portion 42 could further have a double open-ended channel 44 running through it sized to securely affix (e.g., via medical grade adhesive or other suitable attachment means—not shown) to the proximal needle portion 26 that passes through the double open-ended channel 44. The bonding surface (not shown) of the proximal needle portion 26 could be further sand blasted to create a better bond interface for adhesive attachment to the handle 40.

Figure 4:
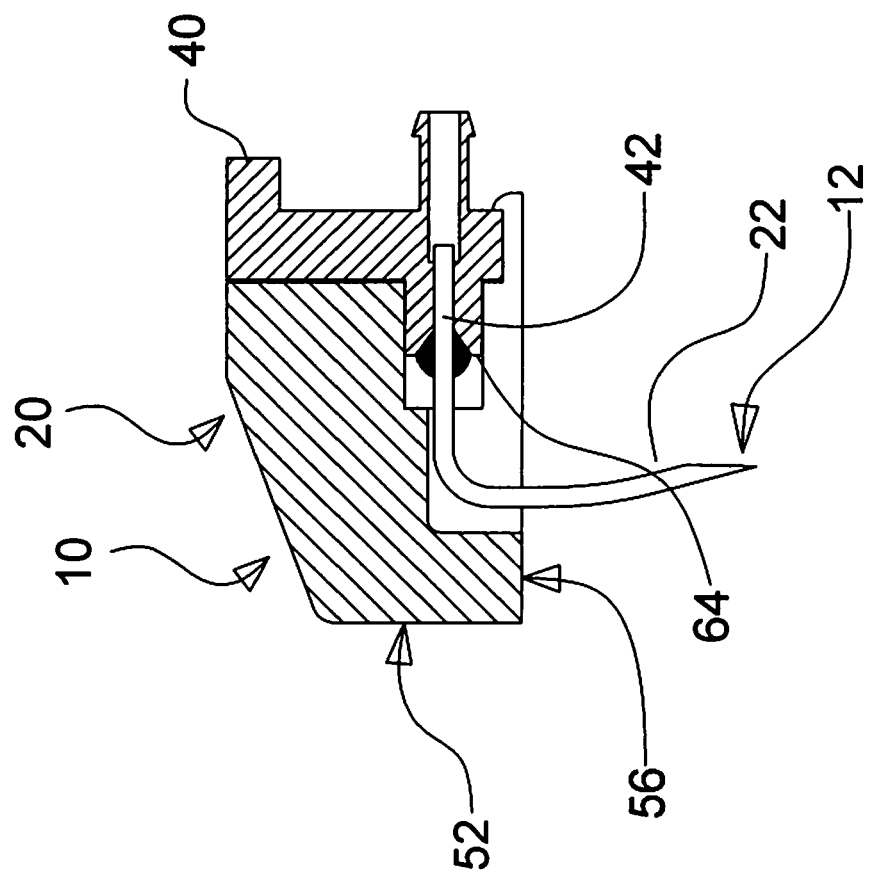
FIG. 4 is substantially a cutaway elevation view of one embodiment of perpendicularly angled hypodermic needle version of the present invention.
Figure 4A:
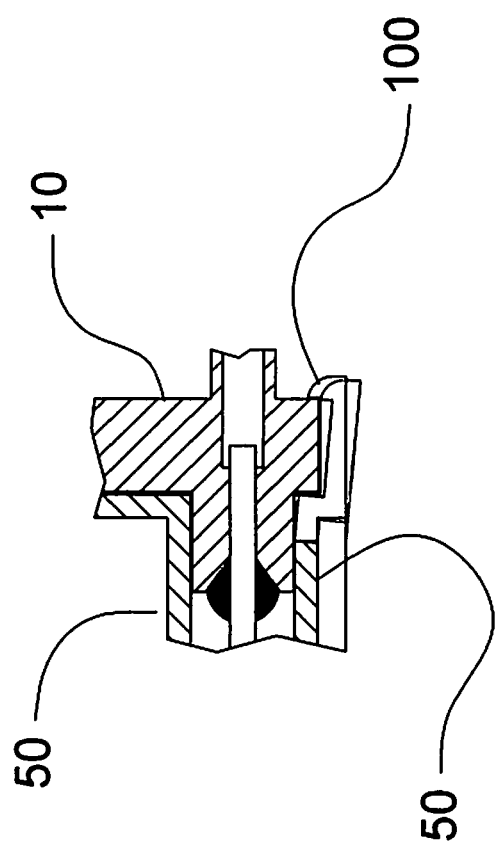
FIG. 4A is substantially a cutaway elevation view of one embodiment of locking mechanism holding the hypodermic needle handle combination in place within the shield.

As substantially shown in FIG. 4, a part of the cylinder portion 42 could further extend past its end connection to the handle 40 to be substantially rotatably grasped by an open-ended, open-sided slot 64 generally provided the shield 50. The slot 64 could have at least one open end into which could be inserted the cylinder portion 42 of the handle 40 into the slot 64 to rotatably attach handle/needle to the shield 50 during the manufacture of the invention 10. As substantially shown in FIG. 4A, a clip or other type of suitable locking mechanism 100 could be employed to hold the handle 10 within its rotatable relationship with the shield 50.

When generally rotatably grasped by the shield 50 in this manner, the handle 40 could be further manipulated by an operator (not shown) to substantially rotate the distal needle portion 24 (e.g., around its centerline longitudinal axis) between its operating (e.g., vertical) position 12 (e.g., descending down and away from the bottom 56 or underside of the shield's skin pad portion 52 in a perpendicular orientation to the bottom 56, the needle tip 30 being held away from the shield's bottom 56) and the needle's stored or storage (e.g. horizontal) position 14 (e.g., placing the needle tip 30 next to the shield's bottom 56).

Figure 5:
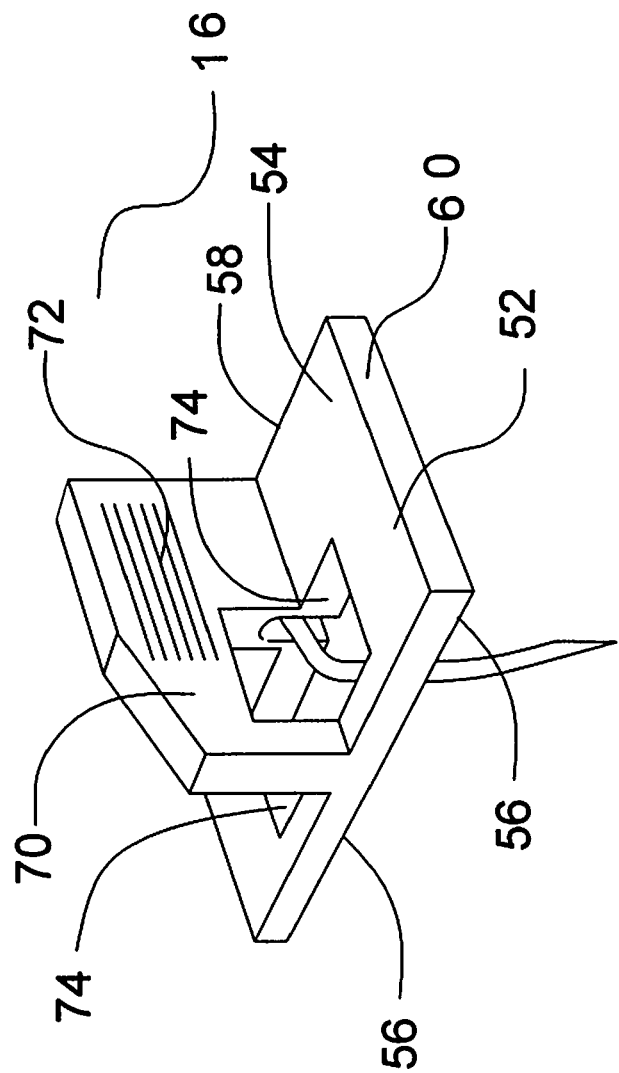
FIG. 5 is substantially an upper side perspective view of one embodiment of the shield of the present invention.
Figure 6:
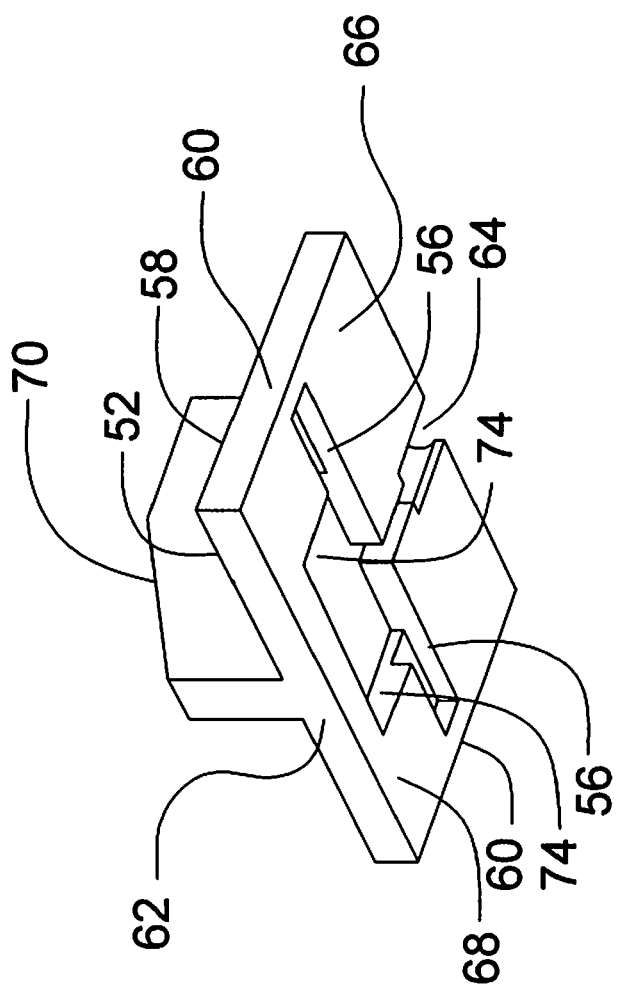
FIG. 6 is substantially an underside perspective view of one embodiment of the shield of the present invention.

As substantially shown in FIGS. 5 and 6, the shield 50 could be made of suitable material (e.g., molded plastic or the like) that has a generally horizontal plate forming a skin pad portion 52. The skin pad portion 52 could comprise a top 54, a bottom 56 connected together by two side edges 60, a forward edge 62 and a following edge 58. The bottom 56 could further be bifurcated into a left (or first) side 66 and a right (or second) side 68. In one version of the shield 50, a vertical blade 70 may arise in a perpendicular fashion from the midline of the top 54 to be generally grasped by an operator (not shown in the drawings) to suitably manipulate the shield 50 for positioning and operation of the invention 10. Additionally, the vertical blade 70 may have a plurality of small horizontal grooves 72 to facilitate better traction for the practitioner's gloved fingers.

The vertical blade 70 may bisect the skin pad portion's top 54 to substantially provide a pair of top surfaces to which tape (not shown) may be applied to hold the shield 50 in position over the patient's injection site (not shown.) The shield 50 may further have one or more shield apertures 74 continuously connecting the top 54 to the bottom 56 that allows the location of the distal needle portion 24 relative to the bottom 56 to be observed through the shield's top 54.

As noted above, the shield 50 may further have the double open-ended/open-sided slot 64 that rotatably grasps the cylinder portion 42 of the handle 40. In one embodiment, wherein the bent hypodermic needle 22 has a perpendicular relationship between the proximal needle portion 26 and the distal needle portion 24, the slot 64 could be located along the shield's bottom 56 so that the handle 40 is located at the back of the shield 50.

Figure 7:
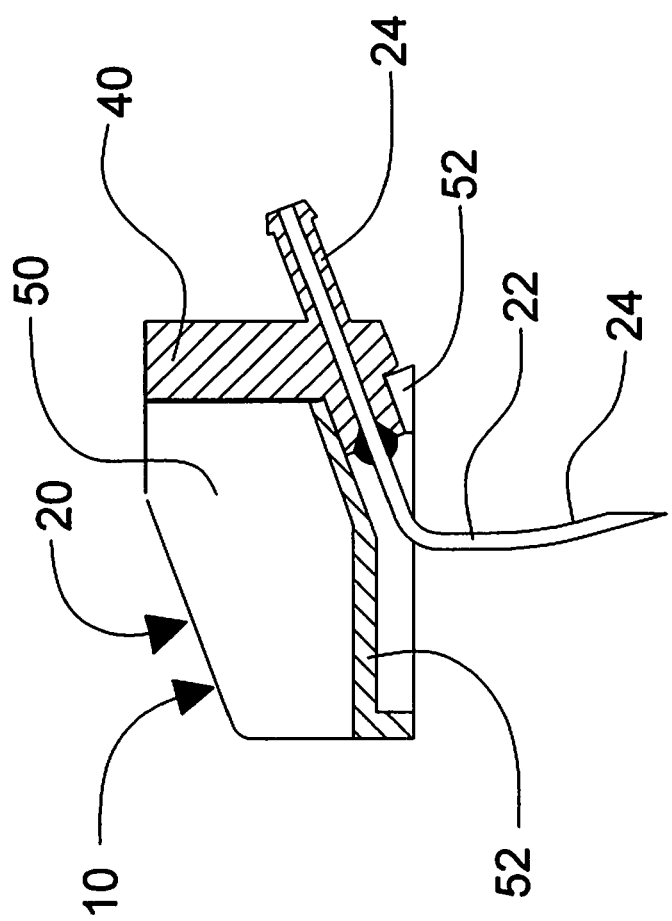
FIG. 7 is substantially a cutaway elevation view of one embodiment of obtuse angle hypodermic needle version of the present invention.
Figure 8:
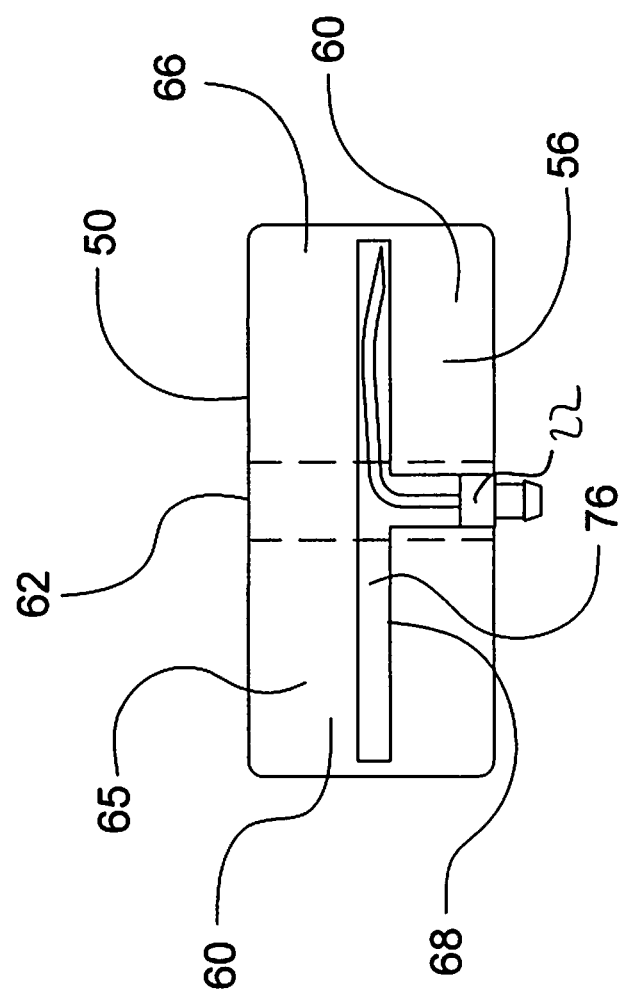
FIG. 8 is substantially an underside view of one embodiment of shield of the perpendicularly angled hypodermic needle version of the present invention.
Figure 8A:
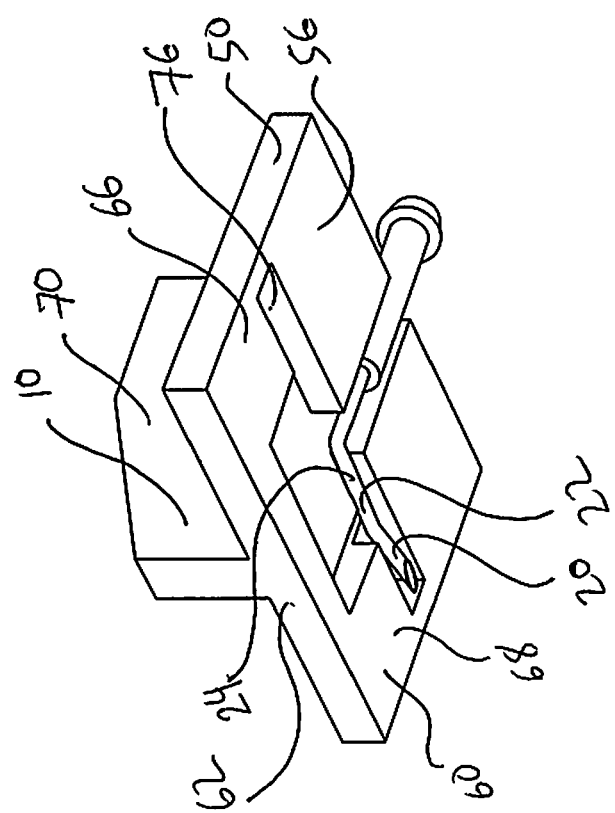
FIG. 8A is substantially an underside perspective view of one embodiment of shield of the perpendicularly angled hypodermic needle version of the present invention.
Figure 9:
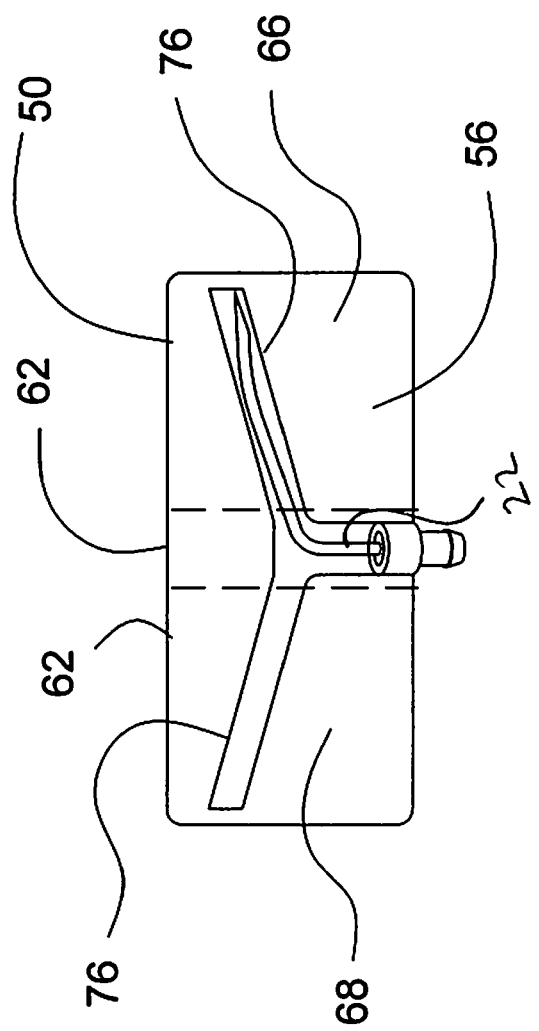
FIG. 9 is substantially an underside view of one embodiment of shield of the obtuse angled hypodermic needle version of the present invention.
Figure 9A:
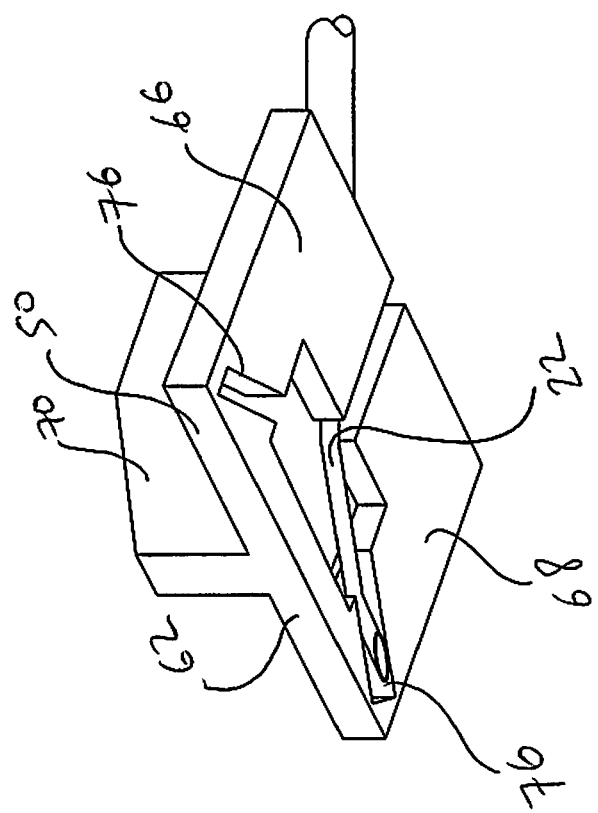
FIG. 9A is substantially an underside perspective view of one embodiment of shield of the obtuse angled hypodermic needle version of the present invention.

As substantially shown in FIG. 7, one possible embodiment wherein the angular relationship between the distal and proximal needle portions 24, 26 is formed upon an obtuse angle, the slot 64 is angularly located upon the shield 50 wherein one slot open end may be found on the bottom 56 (e.g. from where the distal needle portion 24 projects out) while the other slot open end may be proximate to the top 54 of the skin pad portion 52.

As substantially shown in FIGS. 8, 8A, 9 and 9A, the bottom 56 may have one or more cutouts 76 (e.g., one cutout 76 on the bottom's first or left side 66 and another cutout 76 on the bottom's second or right side 68) to receive the distal needle portion 24 when moved into the stored position 14. When the bent hypodermic needle 22 has a perpendicular relationship between its portions, the needle tip 30 of the distal needle portion 24 in the stored position may be found in a cutout 76 that is terminating at one of the skin pad portion's side edges 60.

Figure 10:
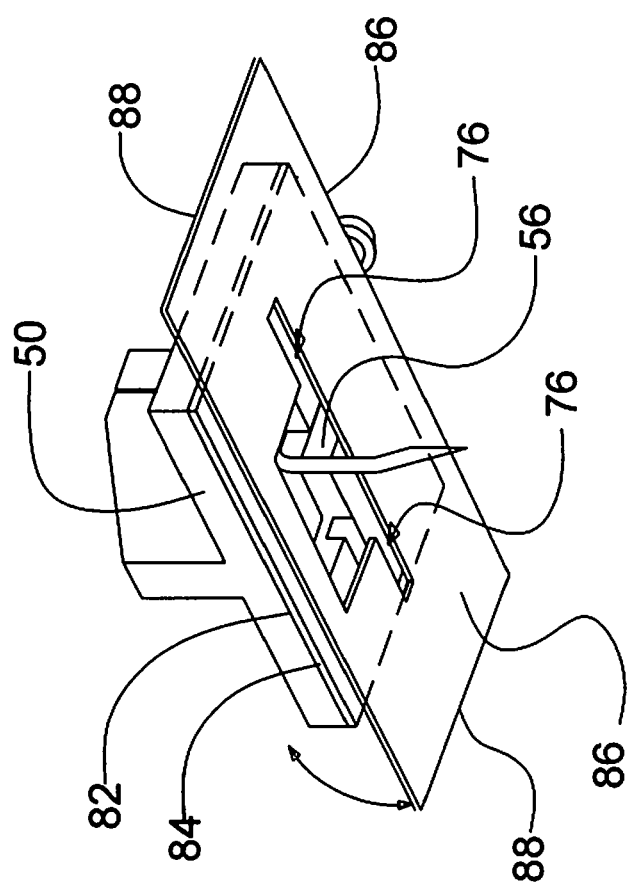
FIG. 10 is substantially an underside view of one embodiment of present invention showing the laminate pad with removable covers.

As substantially shown in FIG. 10, the shield 50 could further comprise a laminated pad 80 attached to the bottom 56. The laminated pad 80 could comprise a first adhesive layer 82 to generally connect the laminate pad 80 to the bottom 56; a compressible padding layer 84 to provide a gentle resting media for the invention support upon the injection site (not shown) for patient comfort; a second low adhesion adhesive layer 86 to reversibly connect the laminate pad 80 to the skin of the injection site; and a removable cover 88 that exposes the second adhesive layer 86 for use when removed from same. The laminate pad 80 itself may have one or more cutouts 76 and like to accommodate the stored position placement of the distal needle portion 24. In this manner, the distal needle portion 24 can be stored in sterile environment within the cutout 76 and be covered by the removable cover 88, thus reducing and simplifying any packaging used for maintaining a sterile and unused bent hypodermic needle 22. By removing the removable cover 88 from the remainder of the laminate pad 80, the distal needle portion 24 is then free to be rotated into its operative position and the invention 10 can be made ready for use.

Figure 11:
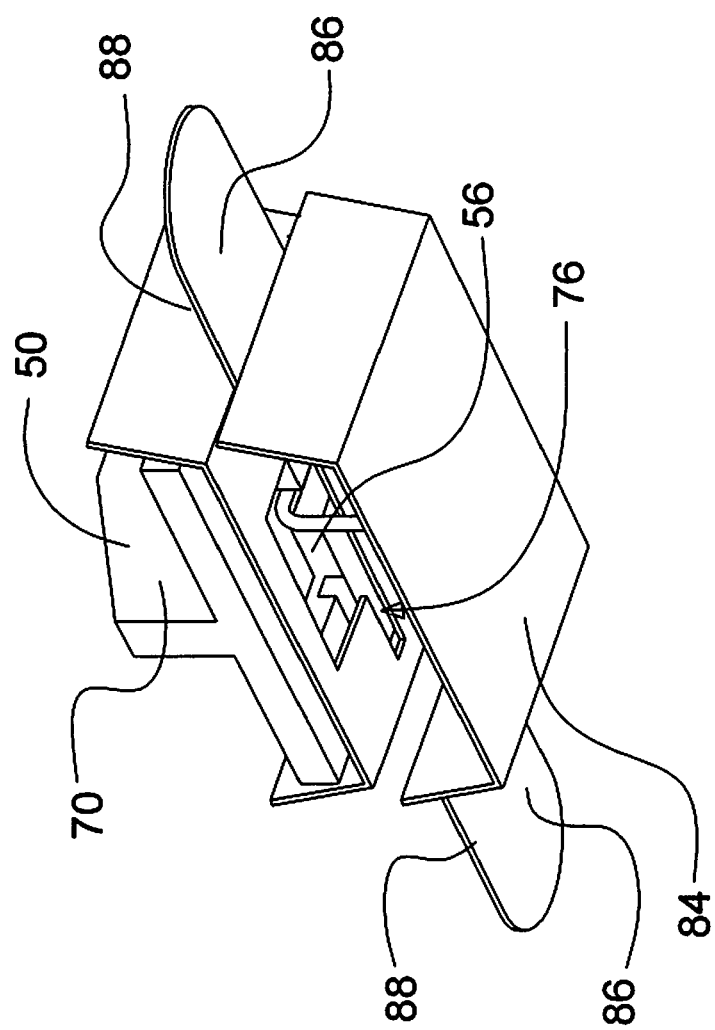
FIG. 11 is substantially an underside view of another embodiment of laminate pad with removable covers.

In another version, as substantially shown in FIG. 11, the removable cover 88, not the compressible padding layer 84, has a second low adhesion adhesive layer 86 attached to it. The adhesive for the second adhesive layer 86 could allow removal of the removable cover from a portion of the compressible padding 84 while allowing the removable cover 88 by one of its edges to attach to an edge portion of the remaining laminate pad 80. This movement could allow the removable cover 88 to generally be peeled back and expose its second adhesive layer 88. The removable cover/second adhesive layer 88 could be applied proximate to the patient's injection site to reversibly attach the invention 10 to the skin of the patient (not shown.) After usage, the removable cover 88 is removed from the patient's skin, generally allowing the invention 10 to be removed from the injection site. After the invention's removal, the distal needle portion 24 can be rotated into the cutout 76 (either the original cutout and/the laminate pad cutout) for disposal. The removable cover 88 can then be fully applied over the remaining laminate pad 80 to seal back in the distal needle portion within the cutout 76 for safe disposal.

Figure 12:
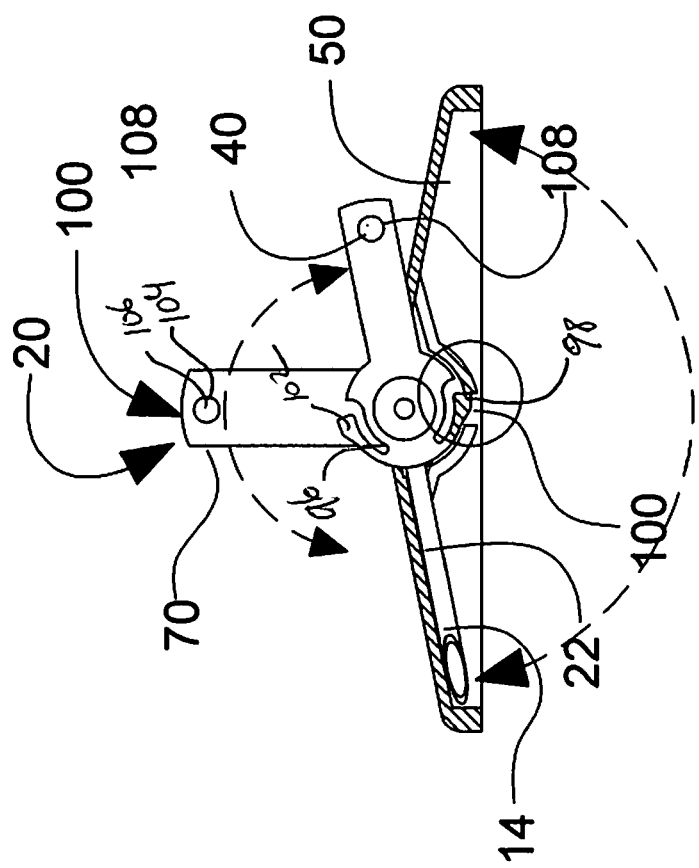
FIG. 12 is substantially an elevation end view showing one embodiment of the locking mechanism of the present invention to hold the needle in position relative to the shield, the position being storage position.
Figure 12:
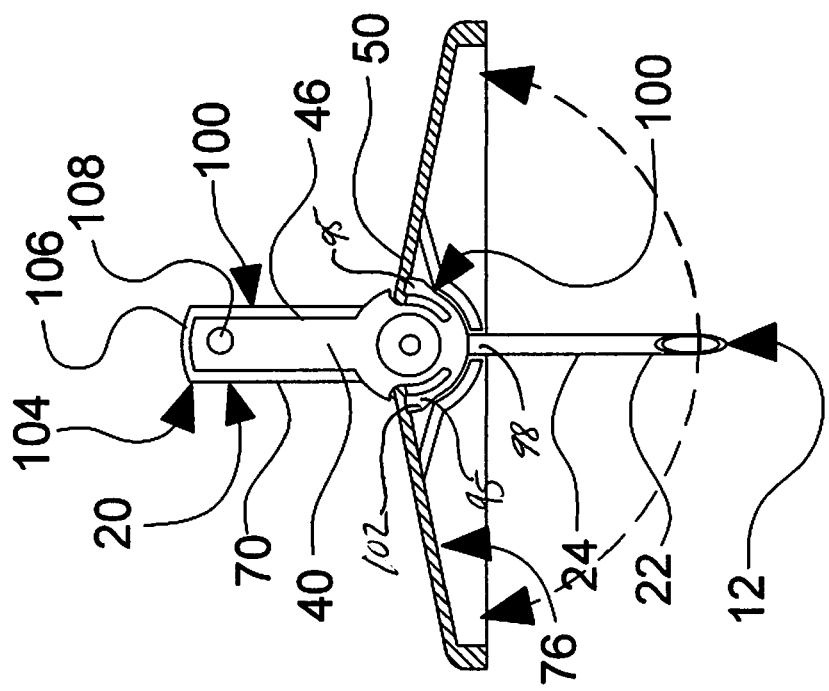

Various embodiments of the invention 10 may have one or more locking mechanisms 100 to help ensure that the distal needle portion 24 when set by the medical practitioner in a desired position (e.g., stored or operating positions 14, 12) substantially stay in the selected position unless the medical practitioner specifically moves the distal needle portion 24 out of that position. As substantially shown in FIGS. 12 and 12A, one such locking mechanism embodiment could have the handle with two arms, each arm having a barb 102. When the handle is rotated relative to the shield 50, the barb is biased by the arm to projecting into a biasing aperture 98 to hold the needle in the stored position 14 within a cutout 76 of the shield. When the barb 102 is not biased into the biasing aperture 98, the hypodermic needle 22 can be held in the operating position 12. This locking embodiment may further make use of a detent-type locking mechanism 104 that operates with the vertical blade 72 and the handle 40. This could allow a ball projection 106 on a leading edge 46 of the handle 40 to reversibly mate with a respective notch or other indent 108 suitably located upon a following edge of the vertical blade 70 to generally hold the distal needle portion 24 in the operating position 12 (e.g. descending down and away from the bottom 56 in a generally perpendicular manner/aligning up and holding the vertical blade 70 with the handle 40 in a planar relationship.)

Figure 12B:
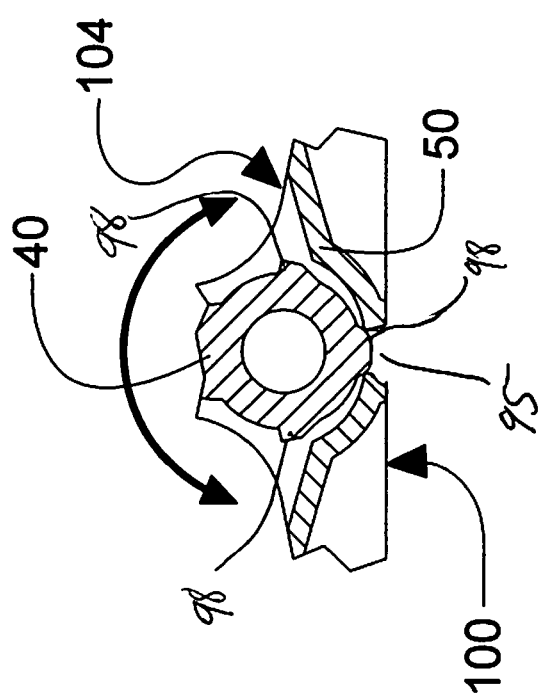
FIG. 12B is substantially an elevation end view showing another embodiment of the locking mechanism of the present invention to hold the needle in position relative to the shield.

As substantially shown in FIG. 12B, another locking mechanism embodiment could lack the arms 95 and have instead a series barbs 98 projecting outward from the needle handle portion to directly engage the biasing aperture 98. One barb 98 can set the needle into its operating position while the other two barbs 98 can hold the needle into its stored position.

Figure 13:
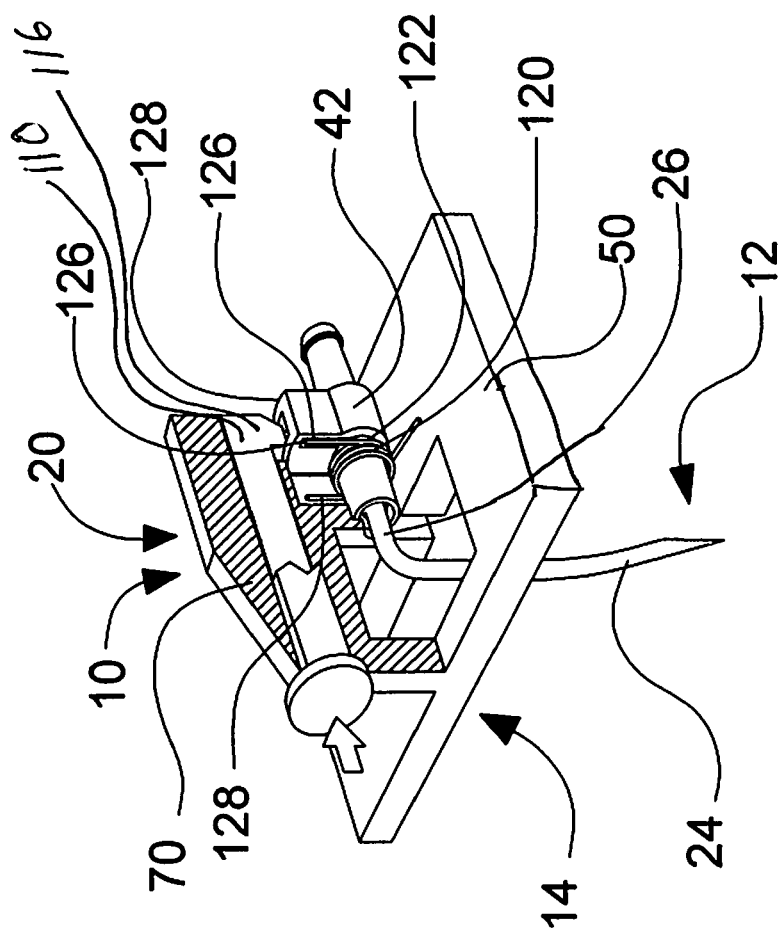
FIG. 13 is substantially a perspective cutaway view of one embodiment of the key-based locking mechanism of the present invention to hold the needle in position relative to the shield.

As substantially shown in FIG. 13, another locking mechanism 100 could make use of a biased key 110, a portion of which could movably pass though the vertical blade 70 that connects the vertical blade leading edge with a following edge of the vertical blade 70. This biased key 110 could have a first key end 114 that forms a grip that may be grasped by the operator (not shown) for key manipulation while the second key end could form a key tip 116 that reversibly engages a suitable handle aperture 118 found on the handle 40 (e.g., the handle's leading edge) to hold the handle 40 in planar alignment with vertical blade 70. The biased key 110 could be biased (e.g., by separate spring, a resilient member of the key, or the like) to project the key tip 116 out past the following edge to allow the key tip 116 to engage (reversibly) the handle's aperture 118. By grasping the grip and pulling the biased key 110 against the biasing force, the key tip 116 could be moved toward the vertical blade 70 and out of/away from the aperture 118 to substantially allow the handle 40 to be moved out of planar relationship with the vertical grip 70 (e.g. moving the needle tip 30 toward its stored position 14.)

This type of locking mechanism embodiment could further feature a bias device 120 that could be used in conjunction with the locking mechanism(s) 100. Such a bias device 120 could be a coiled spring 122 whose two ends generally extend outwards into arms 128. The distal needle portion 24 could be inserted into the center of the coil spring 122 to load the coil spring 122 upon the handle's cylinder portion 42. As the handle 40 is rotatably attached to the shield 50, the coiled spring 122 is sandwiched between the shield 50 and the handle 40. A first vertical recess 124 in the vertical blade 70 could accept one arm 128 of the coil spring 122 while a second vertical recess 126 in the leading edge of the handle 40 accepts the remaining arm 128. If both arms 128 are oriented in parallel when the coil spring 122 is in a rest state, the bias of the coil spring 122 could be used to move the handle in parallel alignment with the vertical blade (and rotate the distal needle portion away from the stored position.) If the arms 122 are oriented perpendicularly to (or even in an obtuse angular relationship with) one another in a rested state, the coil spring 122 could be used to substantially propel the distal needle portion from its operating position 12 towards its stored or storage position 14 (e.g. when a locking mechanism [not shown] holding the handle 40 and vertical blade 70 in planar alignment is released.)

Figure 14:
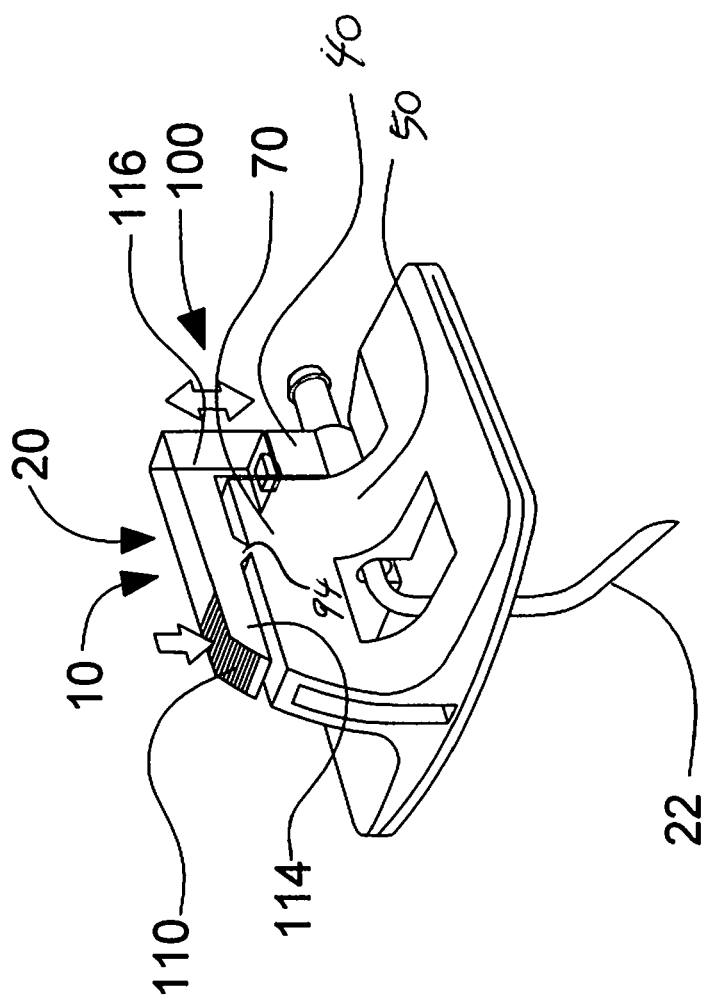
FIG. 14 is substantially a perspective cutaway view of one embodiment of another key-based locking mechanism of the present invention to hold the needle in position relative to the shield.

As substantially shown in FIG. 14, another embodiment of key-based locking mechanism 100 could have the biased key 114 attached by a fulcrum 40 to the shield 50 where in the key tip holds the needle in rotational place relative to the shield 50 (e.g., the operating position.). By pressing down on the grip 114 towards the shield 50, this pivoting action upon the fulcrum 94 causes the key tip to pivot upwards and disengage from the handle 70 to allow a rotation of the needle 22 towards its stored position.

Although not shown, it should be noted that a wide variety and number of locking mechanisms 100 (with or without biasing device[s] 120) can be used to hold the distal needle portion in a storage position(s) or an operative position. The biasing device[s] 120 can be used to move the handle/distal needle portion between the two types of positions. For example, the distal needle portion could be initially packed in a lirst storage position on the left side bottom of the skin pad portion. A detent mechanism between the handle and following edge of the left-side of the shield could hold the distal needle portion in that first storage position until operator intervention occurs. The operator's movement of the handle (e.g. assisted by a biasing coil spring with parallel arms located axial between the shield and the handle) could move the distal needle portion into the operative position wherein a second locking mechanism (detent and/or key types) could then hold the handle (and hence the distal needle portion) in operative position. When the second locking mechanism is released/overcome (and the bias of the coil spring is overcome as well) the handle cab could be used to rotate the distal needle portion towards to the right side bottom of the skin pad portion. At this other or second stored position a third detent locking mechanism now holds the handle so that the needle tip is held proximate to the right side bottom of the skin pad portion. In this second storage position, the invention is ready for safe and proper disposal. A wide variety and selection of locking devices and/or biasing devices can be employed separately and together by the invention and still be considered to be well within the purview of the invention.

Figure 15:
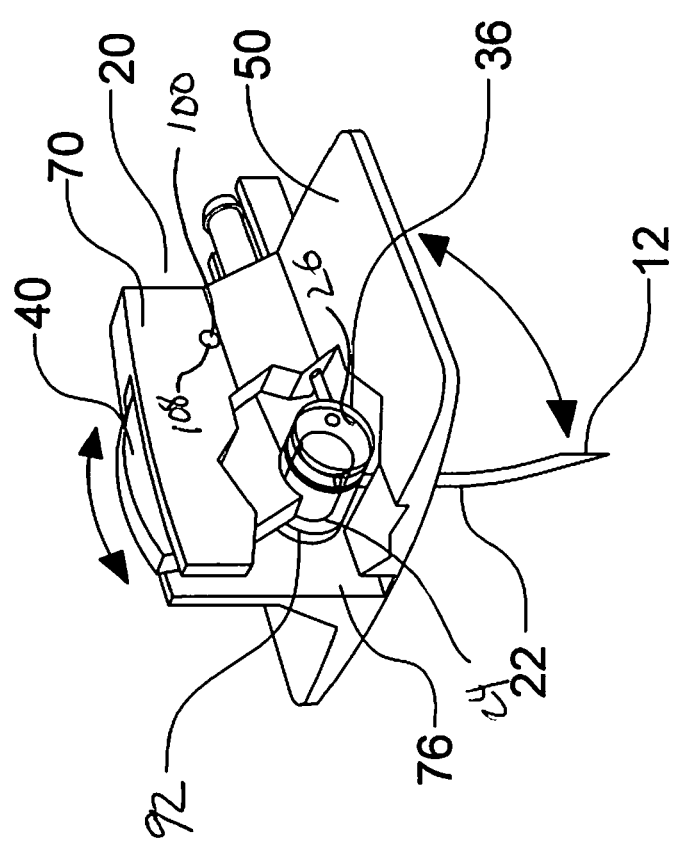
FIG. 15 is substantially a cutaway side elevation view of one possible embodiment of the present invention wherein the distal portion of the needle generally folds along the length of the shield.
Figure 15A:
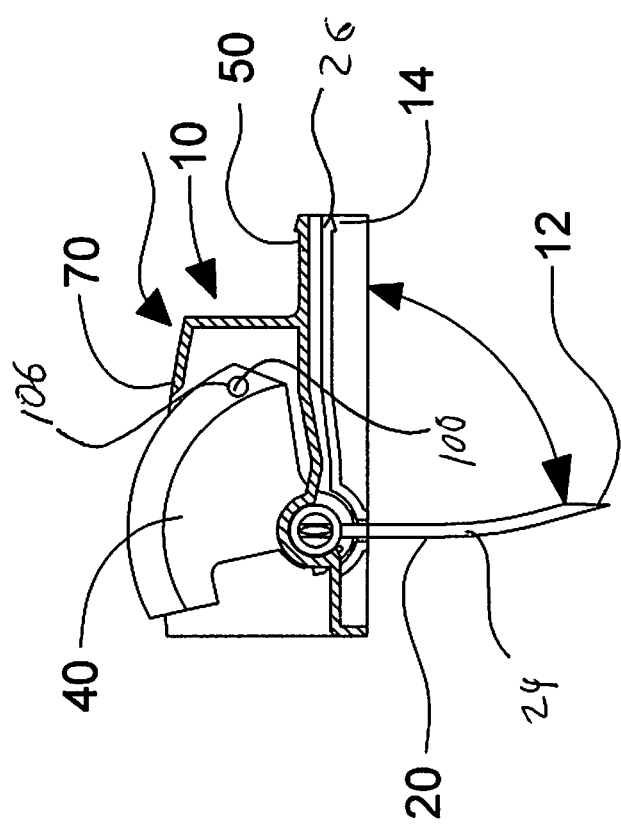
FIG. 15B is substantially a cutaway side elevation view of one possible embodiment of the present invention wherein the needle generally folds along the length of the shield, showing the needle in the stored position.
Figure 15B:
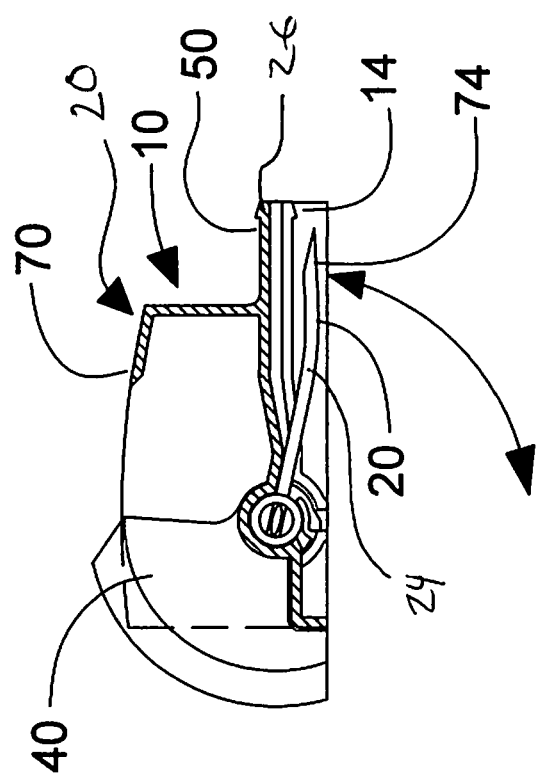

As substantially shown in FIGS. 15, 15A and 15B, one possible embodiment could have the distal needle portion 24 be continuously and rotatable attached to the respective proximal needle portion 26 by a rotatable connection 92 as selected by those having ordinary skill in the art. The proximal needle portion 26 generally could be fixed in place in the shield and substantially would not rotate or otherwise move. The proximal needle portion 26 is held fixed relative to the shield 50 while allowing the distal needle portion 24 to be rotated relative to the proximal needle portion 26 and the shield 50. The distal needle portion 24 can be rotated by a handle 40 that is attached to it to move the distal needle portion 24 from a standard operating position 12 to a storage position 14 wherein the distal needle portion 24 and proximal needle portion 26 are placed proximate to one anther in a parallel configuration. In this manner, the distal needle portion 24 moves along the length, rather than width of the shield 50.

The handle 40 and vertical blade 70 can be further equipped with a mutual locking mechanism 100, wherein a notch 108 on the vertical blade 70 can engage a ball projection on the handle 40 to hold the distal needle portion 24 in its operating position 12 until otherwise moved by an operator (not shown.)

As substantially shown in FIG. 16, one possible embodiment for the process or method 200 for operating the invention 10 could start with step 202, selecting and preparing injection site. In this step, the health care professional generally determines and injects where the injection site (e.g. upon which the invention is used) should be on the patient. For a Huber type needle embodiment, the injection site should be over a port or a septum. The healthcare care professional can then swab down the injection with anti-microbial prep. At substantial competition of this step, the process 200 could proceed to step 204, preparing the device.

In step 204, preparing the device, in at least one embodiment, the needle/shield is already attached to the medical fluids handling device (e.g., a syringe is attached to the needle/shield) and is packaged as one unit within protective sterile packaging. In one or more other possible embodiments, the needle/shield combination is packaged by just by itself. In any case, the protective sterile packaging is breached and the invention with or without attached medical fluids handling device is removed from the packaging.

As the particular embodiment may dictate, the hypodermic needle's connection end may be then attached to medical fluids handling device (e.g., as used for drug delivery/infusion with chemotherapy.) In other embodiments involving a syringe, the syringe may be loaded with suitable liquid utilizing the needle.

In those embodiments utilizing a laminate pad, the health care operator could grasp the reversible cover and pull most of it off from the laminate pad to expose the (e.g. laminate) cutout containing the distal needle portion. The vertical blade could be grasped by its grooves to allow the handle to be moved away from the vertical blade. In doing do, a locking device if provided, may need to be first disengaged or overridden and a bias device if provided could be prejudiced against to move the handle's leading edge up with one of the skin pad portions following edges (left/right). This action could generally place the handle in a planar alignment with the skin pad portion to substantially rotate the distal needle portion into an operative position. If a locking device is used, it or second locking device could be engaged to hold the distal needle portion in the operative position. After this step is completed, the process could proceed to step 206, injecting the needle.

In step 206, injecting the needle, the needle tip is introduced to the injection site. Exposed second adhesive layer (if found on exposed laminate pad or removable covers) can attach to the skin help hold the skin pad portion proximate to the injection site. Tape strips can be applied to tops of the skin pad portion/patient's skin to attach the shield to the injection site as well. Once the invention is secured at the injection site, step 206 may be seen as being substantially completed and the process 200 could proceed to step 208, transferring fluids through the needle.

In step 208, transferring fluids through the needle, the medical machinery attached to the needle is activated or otherwise allow to operate and pass fluids through the needle (e.g., into and/or form the patient). Once this step is substantially completed, the process 200 could proceed to step 210, removing and disposing of the device.

In step 210, removing and disposing of the device, in this step the medical machinery attached to the needle is deactivated or otherwise made to prevent further fluid transmission through the bent hypodermic needle. The hypodermic needle (e.g., the invention itself) is removed from the injection site (e.g. if provided the removable cover with the second adhesive layers are pulled back and away from the skin, along with the tape strips. The connected end is disconnected from the medical machinery/device. The handle could be grasped and otherwise moved (e.g. by a biasing device or like) to be aligned with one of following edge of the skin pad portions to rotate the distal needle portion (e.g., needle tip) out of its operative position and into a stored position (e.g., distal needle portion into a cutout [e.g., the original cutout or another cutout] wherein the needle tip is placed next to the bottom.) In making this rotation movement, second locking device (if provided) may be disengaged or otherwise overcome to substantially allow this rotational movement and/or a biasing device engages/is overcome to further influence the distal needle portion's rotation movement at this point. The first locking device may be reengaged (or if the distal needle portion goes to another different laminate pad cutout a third locking device may be engaged) to hold the distal needle portion within the cutout (the originally used or other cutout.) The reversible cover could be fully returned upon the laminate pad to seal and otherwise enclose the distal needle portion with in the cutout for safe and effective disposal in a manner that may be seen as significantly reducing unwanted and/or accidental, post-use needle-sticks. As this step is completed, the process could return to step 202 as required.

CONCLUSION

Although the description above contains many specifications, these should not be construed as limiting the scope of the invention but as merely providing illustrations of some of the presently preferred embodiments of this invention. Thus, the scope of the invention should be determined by the appended claims and their legal equivalents rather than by the examples given.

What is claimed is:

1. A hypodermic needle that rotatably connects to a shield comprising:
   (A) a hypodermic needle bent into a distal needle portion and a proximal needle portion, the distal needle portion further having a needle tip, the proximal needle portion having a connection aperture;
   (B) a shield that comprises at least a skin pad portion and a vertical blade, the vertical blade being permanently set at a non-parallel orientation to the skin pad portion, the proximal needle portion being rotatably held within a portion of the shield in a manner that allows the distal needle portion to be placed directly underneath the skin pad portion and to be moved between an operative position that locates the distal needle portion in a parallel orientation to the vertical blade so as to place the needle tip away from the skin pad portion and a stored position that locates the distal needle portion at a non-parallel orientation to the vertical blade and has the needle tip of the distal needle portion placed proximate to the skin pad portion wherein the skin pad portion is not bent or folded around the distal needle portion and the entire distal needle portion remains directly underneath the skin pad portion when moved between the operative and stored positions.

2. The hypodermic needle that rotatably connects to a shield of claim 1 that further comprises a handle, the handle connects to the proximal needle portion.

3. The hypodermic needle that rotatably connects to a shield of claim 2 wherein at least a portion of the handle is rotatably held by the skin pad portion.

4. The hypodermic needle that rotatably connects to a shield of claim 2 further comprising a biasing member that acts upon the handle and the skin pad portion to move the distal needle portion between an operative position and a stored position.

5. The hypodermic needle that rotatably connects to a shield of claim 1 further comprising a non-tape locking device formed by the shield and handle that reversibly holds the distal needle portion in the operative position.

6. The hypodermic needle that rotatably connects to a shield of claim 1 further comprising a locking device that holds the distal needle portion in the stored position.

7. The hypodermic needle that rotatably connects to a shield of claim 6 wherein the stored position is at least one of two locations, a first location that is the left side of a bottom of the skin pad portion of the shield or a second location that is the right side of the bottom of the skin pad portion.

8. The hypodermic needle that rotatably connects to a shield of claim 1 wherein the shield further comprises of one or more shield apertures that allow the observation though the shield of the position of the distal needle portion relative to a bottom of the skin pad portion.

9. The hypodermic needle that rotatably connects to a shield of claim 1 wherein the proximal needle portion is perpendicularly oriented to the distal needle portion, the proximal needle portion being rotatably held by the shield to be located in a position that is parallel to a top of a skin pad portion and where the entire distal needle portion moves between positions that are located directly underneath the skin pad portion.

10. The hypodermic needle that rotatably connects to a shield of claim 1 wherein the proximal needle portion is held at an obtuse angle relative to the distal needle portion to allow the distal needle portion to be rotatably held by the shield in a non-parallel position relative to the top of the skin pad portion.

11. The hypodermic needle that rotatably connects to a shield of claim 1 further comprising a bottom pad laminate that attaches to a bottom of the skip pad portion of the shield, the bottom pad laminate having at least one cutout that accommodates at least a portion of distal needle portion.

12. The hypodermic needle that rotatably connects to a shield of claim 11 wherein the bottom pad laminate further comprises an adhesive layer that attaches the bottom pad laminate to an injection site.

13. The hypodermic needle that rotatably connects to a shield of claim 11 wherein the bottom pad laminate further comprises a removable cover encloses the proximal needle portion within the one or more cutouts.

14. The hypodermic needle that rotatably connects to a shield of claim 13 wherein the removable cover has a cover adhesive layer that can attach to an injection site when peeled back from the bottom pad laminate.

\* \* \* \* \*